US00PP17092P2

(12) United States Plant Patent
Hardy

(10) Patent No.: US PP17,092 P2
(45) Date of Patent: Sep. 12, 2006

(54) ***GAILLARDIA* PLANT NAMED 'ORANGES AND LEMONS'**

(50) Latin Name: *Gaillardia×grandiflora*
Varietal Denomination: ORANGES AND LEMONS

(76) Inventor: Rosemary Hardy, Hardy's Cottage Garden Plants, Freefolk Priors, Whitchurch, Hants (GB), RG28 7NJ ( * ) Notice: Subject to any disclaimer, the term of this patent is extended or adjusted under 35 U.S.C. 154(b) by 76 days.

(21) Appl. No.: 10/983,769

(22) Filed: Nov. 9, 2004

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Louanne Krawczewicz Myers

(57) ABSTRACT

A new cultivar of *Gaillardia* named 'ORANGES AND LEMONS', an herbaceous perennial, that is distinguishable by an erect, compact habit, large composite planar sterile inflorescences which are composed of ray florets which are orange and yellow in color and disc florets which are orange in color. In combination these traits set 'ORANGES AND LEMONS' apart from all other existing varieties of *Gaillardia* known to the inventor.

3 Drawing Sheets

Botanical designation: Genus: *Gaillardia*. Species: ×*grandiflora*.
Denomination: 'ORANGES AND LEMONS'.

BACKGROUND OF THE INVENTION

The present invention relates to a new and distinct cultivar of blanket flower, an herbaceous perennial that is grown for use as an ornamental landscape and container plant. The new invention is known botanically as *Gaillardia×grandiflora* and will be referred to hereinafter by the cultivar name 'ORANGES AND LEMONS'. *Gaillardia* is in the family Compositae, under which the commonly referred to "flower" is actually the inflorescence, and is made up of smaller ray florets and disc florets. The ray florets themselves have the appearance of "petals".

'ORANGES AND LEMONS' arose in the summer of 2002 at the inventor's nursery in Hampshire, England as a single chance seedling which was discovered, isolated and then asexually propagated by the inventor as described herein.

The inventor had grown a crop of plants of the variety *Gaillardia* 'Dazzler' (unpatented), hereinafter referred to as 'Dazzler', from commercially available seed of 'Dazzler' which the inventor had sown in February 2002. In June or July 2002, by which time the seedlings of 'Dazzler' had been transplanted into 9 cm diameter containers and were in flower, the inventor observed a single plant which displayed larger inflorescences with an uncharacteristic orange coloration of the ray florets. Each ray floret was observed to be approximately twenty-five percent longer and broader than the typical ray floret of 'Dazzler'. The inflorescences themselves were observed to be flat or planar rather than concave as is typical of 'Dazzler'.

The female parent of 'ORANGES AND LEMONS' is *Gaillardia* 'Dazzler' (unpatented). The male parent plant is unknown. 'ORANGES AND LEMONS' differs from the parent plant, *Gaillardia* 'Dazzler' in respect of the coloration of its ray florets, the size and form of each inflorescence, the overall height and habit of a mature plant, and fertility or sterility. Specifically, the ray florets of 'ORANGES AND LEMONS' are colored orange and yellow, whereas the ray florets of 'Dazzler' are colored predominantly red; an individual inflorescence of 'ORANGES AND LEMONS' is approximately twenty-five percent larger than an individual inflorescence of 'Dazzler' and is also flat rather than concave in form; a mature plant of 'ORANGES AND LEMONS' is 10 cm to 20 cm taller than 'Dazzler' and is also more stiffly erect; and 'ORANGES AND LEMONS' is sterile whereas 'Dazzler' is fertile and sets viable seed.

The first asexual reproduction of 'ORANGES AND LEMONS' was accomplished in September 2002 when the inventor removed and rooted approximately ten nodal cuttings from the originally discovered and isolated plant. The cuttings rooted successfully and since that time subsequent generations have been determined stable and true to type when compared with the original selection which the inventor has retained.

SUMMARY OF THE INVENTION

The following traits have been repeatedly observed and represent the distinguishing characteristics of 'ORANGES AND LEMONS'. These traits in combination distinguish 'ORANGES AND LEMONS' from all other existing varieties of *Gaillardia×grandiflora* known to the inventor. 'ORANGES AND LEMONS' has not been tested under all possible conditions and phenotypic differences may be observed with variations in environmental, climatic, and cultural conditions, however, without any variance in genotype.

1. 'ORANGES AND LEMONS' has an erect, compact habit.
2. 'ORANGES AND LEMONS' is an herbaceous perennial.
3. 'ORANGES AND LEMONS' exhibits large composite planar inflorescences composed of ray florets which are orange and yellow in color and disc florets which are orange in color.

4. A mature one-year old plant of 'ORANGES AND LEMONS' is approximately 700 mm to 800 mm in height and 600 mm. in width at maturity.
5. 'ORANGES AND LEMONS' is hardy to USDA Zone 5.
6. 'ORANGES AND LEMONS' is sterile.

BRIEF DESCRIPTION OF THE DRAWINGS

The accompanying color drawings illustrate the overall appearance of the new *Gaillardia* cultivar 'ORANGES AND LEMONS' showing the colors as true as is reasonably possible to obtain in colored reproductions of this type. Colors in the photographs may differ from the color values cited in the detailed botanical description, which accurately describes the actual colors of the new variety 'ORANGES AND LEMONS'.

The Drawing labeled as FIG. 1 depicts a one-season old whole plant of 'ORANGES AND LEMONS' grown out of doors in a 2-liter container in Hampshire, England. This Drawing depicts the erect and dense habit of 'ORANGES AND LEMONS'.

Figure 1:
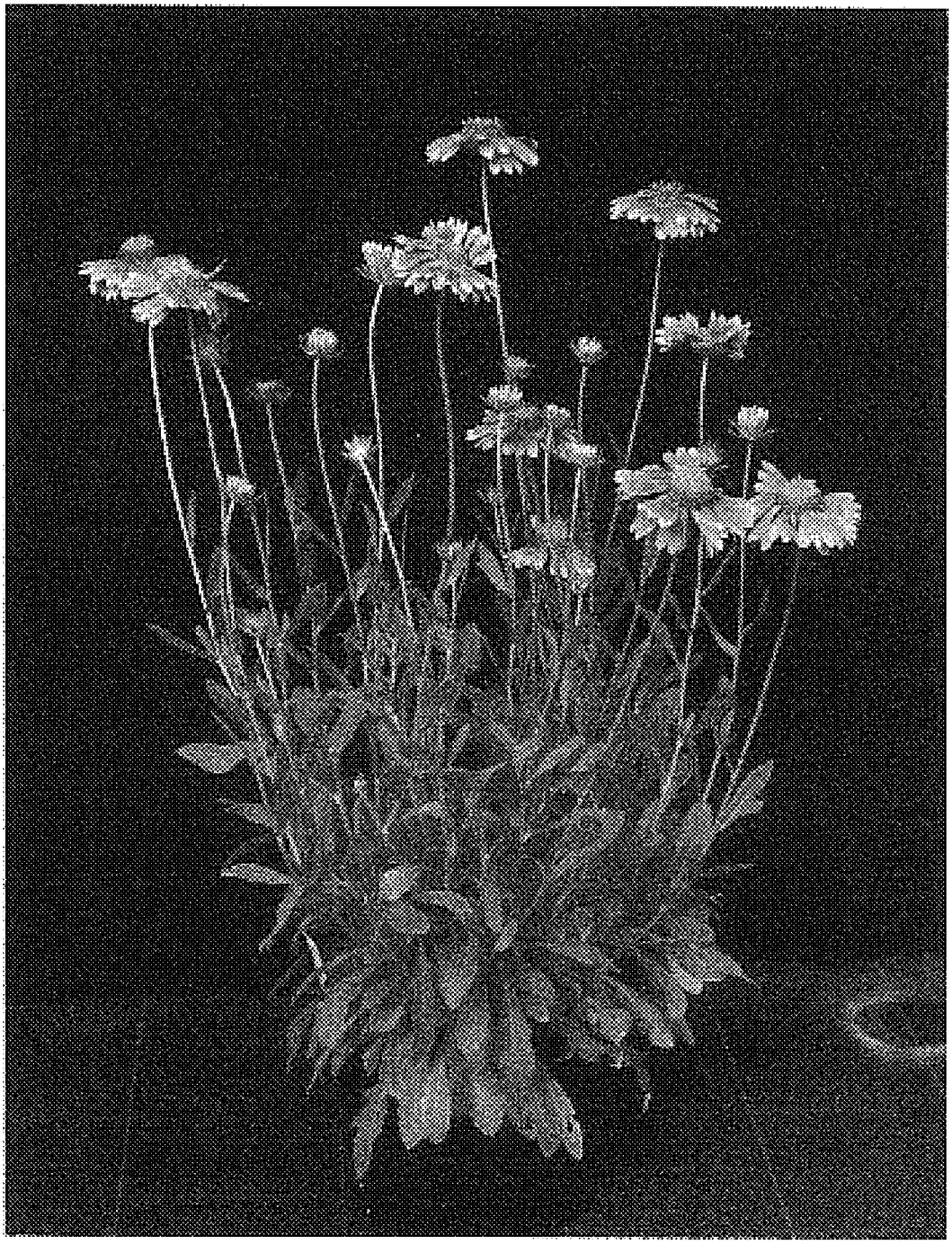
Figure 2:
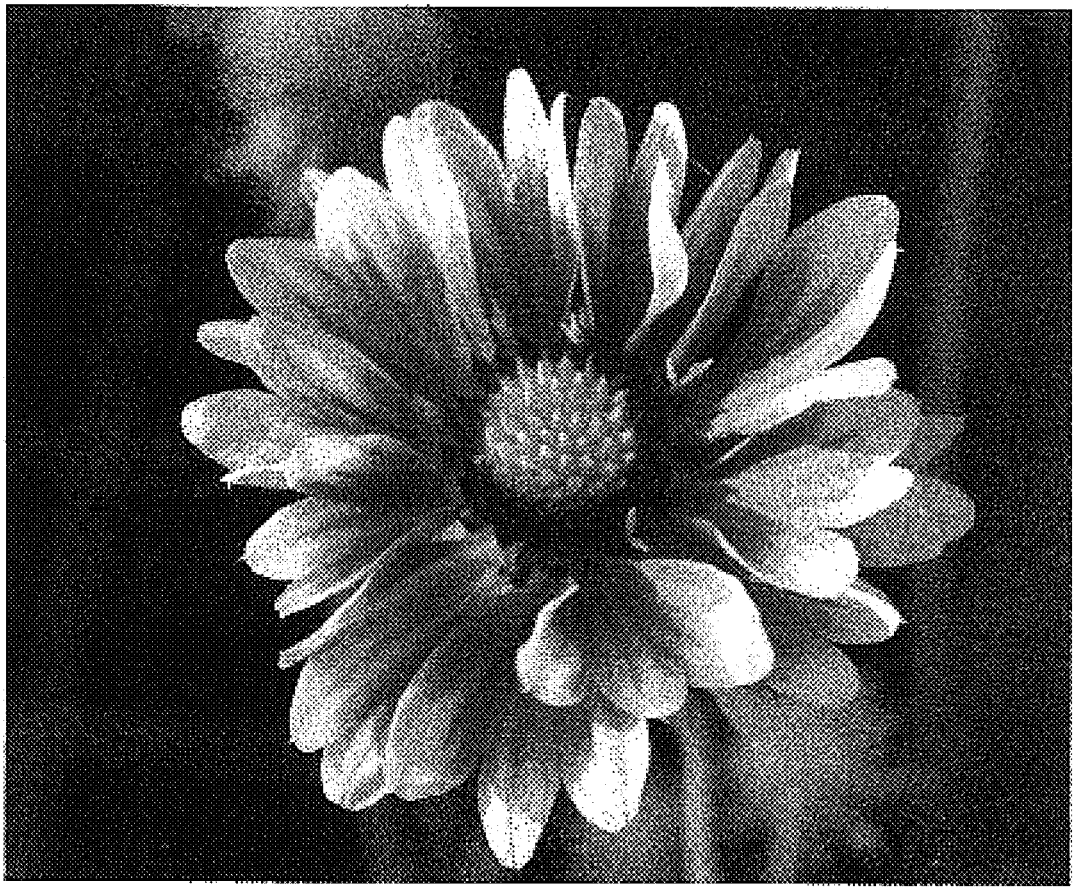

The Drawing labeled as FIG. 2 depicts a close-up view of a single inflorescence of 'ORANGES AND LEMONS'. This Drawing depicts the orange and yellow coloration of the ray florets.

Figure 3:
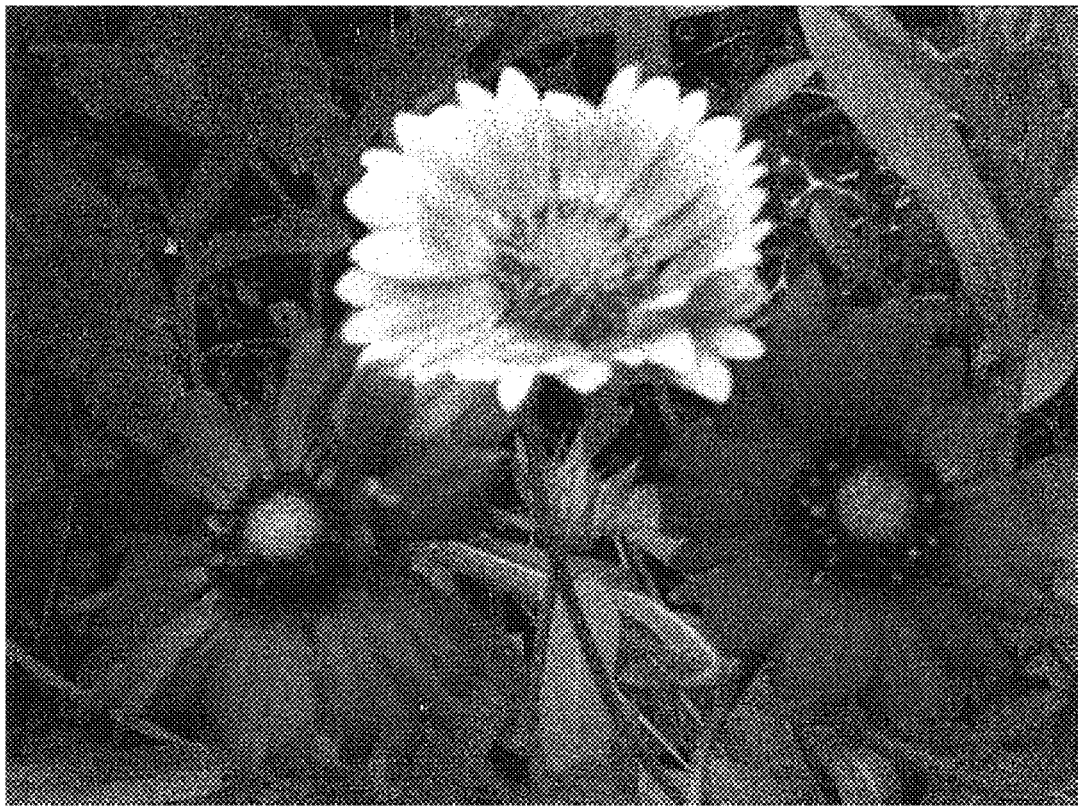

The Drawing labeled as FIG. 3 depicts close-up views of one inflorescence of 'ORANGES AND LEMONS' together with two inflorescences taken from the parent variety, *Gaillardia* 'Dazzler'. This Drawing depicts the contrasting coloration of the ray florets: orange and yellow in 'ORANGES AND LEMONS' and predominantly red in *Gaillardia* 'Dazzler'.

The Drawings were made by printing onto semi-gloss proprietary ink-jet photographic paper images taken with a digital camera and although inflorescence and foliage colors may appear different from actual colors due to light reflectance, they are as accurate as possible by such means.

BOTANICAL DESCRIPTION OF THE PLANT

The following is a detailed botanical description of the new *Gaillardia×grandiflora* cultivar 'ORANGES AND LEMONS'. Observations, measurements, values and comparisons were compiled in Cambridge, England and cross-checked with the inventor's original selection in Hampshire, England. The observations were made during the summer of 2004 utilizing one year old plants grown out-of-doors in a 2 liter container. Color determinations are made in accordance with the 2001 edition of The Royal Horticultural Society Colour Chart from London England, except where general color terms of ordinary dictionary significance are used.

Botanical classification: *Gaillardia×grandiflora* Van Houtte.
Common name: Blanket flower.
Sexuality: Nominally hermaphrodite.
Designated use: Border plant and cut flower.
Soil requirements: Any reasonable garden soil with adequate drainage.
Growing requirements: If grown outside in regions which experience winter freezing, 'ORANGES AND LEMONS' may be started as a cutting during the spring or summer of the previous year, planted out prior to the onset of winter, and flowering will commence typically in May or June according to the region and season. When grown outside in frost-free regions, or in frost-protected greenhouses, 'ORANGES AND LEMONS' will flower virtually all year round and may be started as a cutting (which should be non-flowering) at any time of year.
Light requirements: Sun to part shade.
Propagation method: Softwood cuttings.
Rooting habit: Fine.
Time required to develop roots on an initial cutting: 14 days in mist propagation.
Recommended air temp for cutting to develop roots: 20° C.
Evergreen or deciduous: Semi-evergreen to deciduous.
Dimensions of new variety at maturity: Height approximately 700 mm to 800 mm; width (spread) approximately 600 mm.
Time required for a rooted cutting to reach commercial size: 8–10 weeks to bud and flower in a 1 liter container.
Vigor: More vigorous and a slightly larger plant than the parent, *Gaillardia* 'Dazzler'.
Growth habit: Upright.
USDA hardiness zone: Zone 5.
Susceptibility to particular pests: None has been observed.
Susceptibility to particular diseases: Mild susceptibility to downy mildew (*Peronospora* sp.) and to leaf smut (*Entyloma* sp.).
Resistance to particular pests: None has been observed.
Resistance to particular diseases: None has been observed.
Stem:
- *Height at flowering time.*—590 mm.
- *Diameter.*—4 mm.
- *Internode length.*—45 mm.
- *Branching.*—Prolific, up to five branches produced without pinching. Each branch produces a single terminal inflorescence. Each branch produces further sub-branches from the lower nodes. All sub-branches produce a single terminal inflorescence.
- *Branching angle.*—Approx 30°.
- *Color.*—Green 137D.
- *Cross-section.*—Ribbed, hollow.
- *Pubescence.*—Present, medium density. Hairs eglandular.

Foliage:
- *Leaf shape.*—Obovate to oblong-elliptic, the lower ones occasionally with one or more lobes.
- *Leaf length.*—102 mm.
- *Leaf width.*—25 mm.
- *Leaf arrangement.*—Alternate.
- *Leaf margins.*—Finely serrate-dentate and fairly sparse. Margins not undulate.
- *Leaf division.*—Absent.
- *Leaf apex shape.*—Obtuse, mucronate.
- *Leaf base shape.*—Obtuse to rounded.
- *Leaf color of upper surface.*—Lamina between Green 137A and Yellow-Green 147A.
- *Leaf color of lower surface.*—Lamina between Green 137A and 137B.
- *Leaf pubescence of upper surface.*—Present, sparse, eglandular.
- *Leaf pubescence of lower surface.*—Present, sparse, eglandular.
- *Leaf venation pattern.*—Pinnate.
- *Leaf vein color (upper and lower surfaces).*—Between Green 137D and 139D.
- *Leaf fragrance.*—Absent.
- *Leaf attachment.*—Sessile.
- *Stipules, presence.*—Absent.

Flowering season: May–November in regions with winter freeze; virtually year-round in frost-free regions.

Flowers: (Note: All records below on peduncle and inflorescence, including ray florets and disc florets, relate to the single terminal inflorescence on the stem).

*Peduncle length.*—315 mm.

*Peduncle diameter.*—3 mm.

*Peduncle color.*—Nearest Green 143C.

*Peduncle pubescence.*—Present, moderate density, eglandular.

*Bud height.*—15 mm.

*Bud diameter.*—35 mm.

*Bud shape.*—Bowl-shaped.

*Bud color.*—Ray florets between Yellow 13B and 13C.

*Involucre diameter.*—40 mm.

*Involucral bracts, number.*—28.

*Involucral bracts, length.*—20 mm.

*Involucral bracts, width.*—5 mm.

*Involucral bracts, shape.*—Ovate-triangular.

*Involucral bracts, shape of apex.*—Attenuate.

*Involucral bracts, shape of base.*—Truncate.

*Involucral bracts, margin.*—Entire.

*Involucral bracts, attitude.*—Bracts incurving. Attitude of base of bract pointing slightly downward.

*Involucral bracts, pubescence* (*both surfaces*).—Present, moderately dense, eglandular.

*Involucral bracts, color* (*both surfaces*).—Green 137C.

*Inflorescence.*—Number per plant: 20–25 at first flush of flowering. 40–50 during peak summer flowering.

*Inflorescence.*—Lastingness of an individual bloom on the plant: Ranges from 7–10 days during summer to 10–15 days in spring and fall. May extend to 21 days in late fall.

*Inflorescence persistence.*—Persistent.

*Inflorescence attitude.*—Upright.

*Inflorescence fragrance.*—Faint, spicy smell.

*Inflorescence height.*—33 mm.

*Inflorescence diameter.*—77 mm.

*Ray floret.*—Consists of funnelform corolla tube opening to flat to slightly convex fan shaped ligule. Number per inflorescence: 17. Attitude: Horizontal. Overall length: 37 mm. Corolla tube: Length 3 mm, diameter 1 mm. Base: Truncate. Surfaces (both): Smooth, translucent white 155B. Ligule: Length (excluding corolla tube): 34 mm, Width 20 mm. Shape: Broad ovate, flat to slightly convex at mid-point. Apex: Trifid, occasionally bifid, extending to one third of corolla length. Margin: Entire. Color (upper surface): Basal three quarters 28A or slightly more yellow. Upper one quarter 14A. Color (lower surface): Basal three quarters between 167C and 167D. Upper one quarter 14A. Surface: Longitudinally ribbed. Reproductive organs: Androecium absent; non-functional gynoecium (ovary only) present. Ovary length: 3 mm. Ovary diameter: 1 mm. Ovary color: Green-White 157A.

*Disc.*—Profile: Cushion-shaped. Overall disc diameter: 26 mm. Overall disc depth: 4–5 mm. Color before anthesis: Greyed-Orange 163B. Color at anthesis: Between Greyed-Orange 169A and 169B.

*Disc floret.*—Number: More than 50. Shape: Tubular, consisting of consisting of narrow cylindrical base subtending funnelform corolla tube with five apical lobes. Single disc floret length: 12 mm. Single disc floret width: 3 mm. Surface (outer): Densely pubescent. Surface (inner): Smooth. Corolla tube (cylindrical base): Length 3 mm, diameter 1.5 mm. Color (both surfaces): 157D. Base: Truncate. Corolla tube (funnelform section): Length 9 mm, diameter 2.5 mm at apex. Color (both surfaces): Lobes 42B, becoming suffused 157D towards base. Apical lobes: 5, triangular, 3 mm in length, 1 mm in width. Lobe apex: Acute. Lobe margin: Entire. Reproductive organs: Androecium and gynoecium both present. Number of stamens: 5, united to form a cylinder round the style. Anther length: 4 mm. Anther color: Greyed-Orange 167C. Filament length: 2 mm, fused to form a tube. Filament color: Between Yellow 11A and 11B. Pollen amount: Copious. Pollen color: Yellow-Orange 17A. Stigma length: 11 mm. Stigma diameter: less than 1 mm. Stigma shape: Deeply bifid. Stigma color: Yellow-White 158D. Ovary: length: 2 mm. Ovary: diameter: 1 mm. Ovary color: Green-White 157A but slightly more intense, densely pubescent. Seed: No viable seed produced in any observation; sterile.

It is claimed:

1. A new and distinct cultivar of *Gaillardia×grandiflora* plant named 'ORANGES AND LEMONS' as described and illustrated.

* * * * *